United States Patent
Maher et al.

(10) Patent No.: US 6,515,753 B2
(45) Date of Patent: Feb. 4, 2003

(54) OPTICAL ALIGNMENT IN CAPILLARY DETECTION USING CAPILLARY WALL SCATTER

(75) Inventors: Kevin Maher, Woodside, CA (US); Torleif Ove Bjornson, Gilroy, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 0 days.

(21) Appl. No.: 09/859,749

(22) Filed: May 17, 2001

(65) Prior Publication Data

US 2002/0015147 A1 Feb. 7, 2002

Related U.S. Application Data

(60) Provisional application No. 60/205,520, filed on May 19, 2000.

(51) Int. Cl.[7] .............................................. G01B 11/14
(52) U.S. Cl. ..................................... 356/614; 250/459.1
(58) Field of Search ................................. 356/614, 615, 356/317, 417; 250/458.1, 459.1, 461.1, 461.2, 559.29

(56) References Cited

U.S. PATENT DOCUMENTS

| | | | | |
|---|---|---|---|---|
| 4,330,835 A | * | 5/1982 | Gehm | 364/560 |
| 5,319,442 A | * | 6/1994 | Rosser | 356/375 |
| 6,159,749 A | * | 12/2000 | Liu | 436/527 |

* cited by examiner

Primary Examiner—Jordan M. Schwartz
(74) Attorney, Agent, or Firm—Peter J. Dehlinger; Perkins Coie, LLP

(57) ABSTRACT

The present invention provides for methods and apparatus for locating a capillary channel that is disposed within a lab chip. The method provides for scanning the channel with a light source, monitoring the resulting light at the edges of the lab chip, and interpreting this information whereby the light detected at the edges of the lab chip can be used as a means for characterizing the location of the side walls of the channel within the lab chip. The apparatus provides for a carriage system to which a light source and the lab chip are attached. It also provides for one or more scatter detectors directed towards the edges of the chip and connected to a computer processor for purposes of analysis.

8 Claims, 10 Drawing Sheets

OPTICAL ALIGNMENT IN CAPILLARY DETECTION USING CAPILLARY WALL SCATTER

This application claims the priority of U.S. Provisional Application Ser. No. 60/205,520, filed May. 19, 2000, now abandoned.

TECHNICAL FIELD

The field of this invention is optical alignment of capillaries for detection of luminescence of a solute in a capillary.

BACKGROUND

Microfluidics holds great promise in a number of areas associated with separations, reactions, chemical operations, analysis, sequencing and the like. For many of these areas, it is necessary to detect by optical means a signal emanating from the capillary. While the capillaries are quite small, usually having a width of less than about 200 $\mu$m, compared to molecules and particles, including cells, the width is quite large. Therefore, as these entities pass through a detection zone, it is important that the light beam used for activation be properly directed to the capillary and that the detectors be properly aligned to detect the emitted light from the capillary.

In the systems being developed today, high throughput using low volumes of samples and reagents is of critical importance. Researchers need to rapidly perform and analyze large numbers of chemical and biological operations in a miniaturized, automated format. Current approaches involve the use of lab chips having arrays of capillary or microfluidic networks disposed in a substrate. Within each network, it is possible to independently perform a step, a series of steps or a complete analysis by manipulating small volumes of fluids to conduct chemical operations such as mixing, diluting, concentrating and separating reagents. These manipulations are accomplished through the use of high voltages, pneumatics, and the like.

When applying this technology in the context of microfluidic networks patterned into an array, one frequently wishes to compare results from one network to another. Unless the excitation light sources are providing the same level of irradiation in the same area of the relevant capillary channels, the results will generally not be comparable. Proper alignment of optical detection systems comprised of the excitation source is therefore a necessary requirement.

Further complicating matters is the fact that plastics are becoming the preferred substrate for lab chips. In one aspect, many plastics that are useful for lab chips have a tendency to autofluoresce when exposed to a light source. When light irradiates the capillary walls or plastic substrate in which the capillary is formed, there is a substantial increase in the fluorescent background which substantially increases the noise-to-channel signal ratio. Researchers must be able to reliably distinguish the signal related to the channel contents from the background autofluorescence of the plastic substrate. In another aspect, the channel walls in plastic lab chips are generally not orthogonal to the surface of the chip. Depending upon the incident angle and site of entry of the light source into the channel, the depth of irradiation and the volume irradiated will vary thereby increasing the need for precise and consistent positioning of the light source.

Another challenge related to plastic lab chips arises from the processes commonly used in their manufacture. Prevalent examples of such processes include hot embossing, injection molding, extrusion and the like. In hot embossing, a plastic film is heated and then stamped with microfluidic patterns. With injection molding, plastic is heated to a viscous consistency and then pressed into a specific mold, resulting in a chip having microfluidic patterns. With extrusion, plastic pellets are heated and then forced through a die creating either a single or multiple layer substrate film. This hot film can then be either embossed or run through a gravure roller system which imprints microfluidic patterns onto the heated substrate. Required by each of these processes is the heating of plastic so that it becomes pliable and capable of deformation. The dilemma relative to this heating is that as plastic cools, it shrinks in a non-uniform manner creating irregularities in the substrates and the patterns contained therein.

Current technology related to manufacturing techniques for plastic lab chips has overcome the shrinkage problem with regards to reproducibly generating microchannels having substantially similar profiles and dimensions. However, consistent uniformity with regards to the positioning of these microchannels within specific arrays or patterns has yet to be achieved. This variability is problematic at the microscale level, particularly when trying to align an optical detection system relative to the individual networks. In one critical aspect the optical detection system needs to be mechanically positioned relative to the specific detection zones in each network. In another aspect, the optical properties of plastic polymer chains become anisotropic after the aforementioned shrinkage, contributing to inconsistencies in background autofluorescence and other variables such as refractive indices. Therefore, having an approach to optimally position the irradiation source relative to the microfluidic channels becomes very important in order to minimize background noise and generate reproducible and quantifiable channel signals.

Finally, it is also desirable to have fairly simple optical systems that do not require expensive optical trains to identify the site in the channel to be irradiated.

BRIEF DESCRIPTION OF RELATED ART

U.S. Pat. Nos. 5,545,901 and 5,614,726 describe different ways to position excitation beams in a capillary channel.

SUMMARY OF THE INVENTION

Methods and apparatus are provided for determining the location of a sloped side wall of a microfluidic channel within a lab chip that is composed of a light transmitting substrate. The methods provide for scanning the lab chip with a light source in a plane that is normal to the microfluidic channel, measuring the resulting light produced at one or more edges of the chip, and correlating the resulting light to relative locations within the lab chip. An apparatus is provided which includes a light source, a carriage system for moving the light source relative to the lab chip, one or more scatter detectors, and a computer processor for analyzing the signals from the scatter detectors. Variations are provided where the methods can be used to align optical detection systems at analogous locations relative to similar channels.

DETAILED DESCRIPTION OF THE INVENTION

The present invention provides novel methods and apparatus that are useful for characterizing microfluidic lab chips. This characterization involves determining the location of microfluidic channels within the chip as well as determining areas within different channels where analogous volumes of the channels' contents can be irradiated in a substantially reproducible manner. This characterization is critical for the alignment of optical detection systems in automated high throughput applications.

Figure 1:
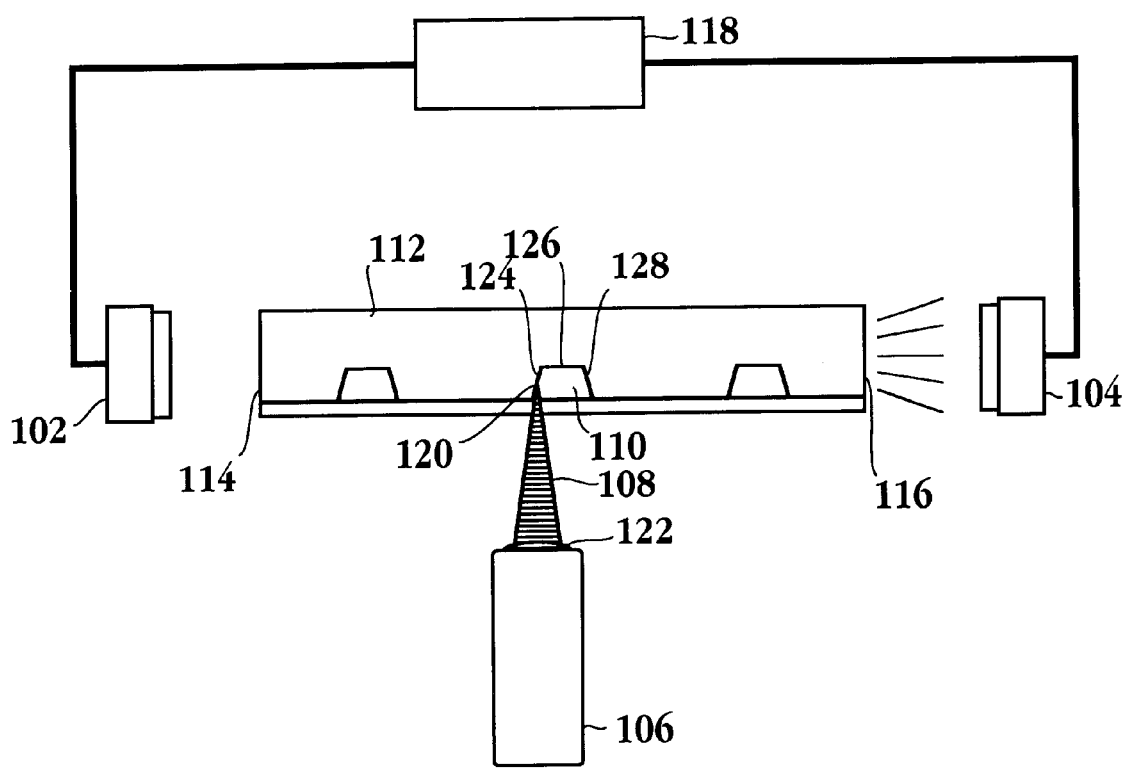
FIGS. 1 and 2 are schematics demonstrating the application of the invention relative to a cross sectional view of a lab chip.
Figure 2:
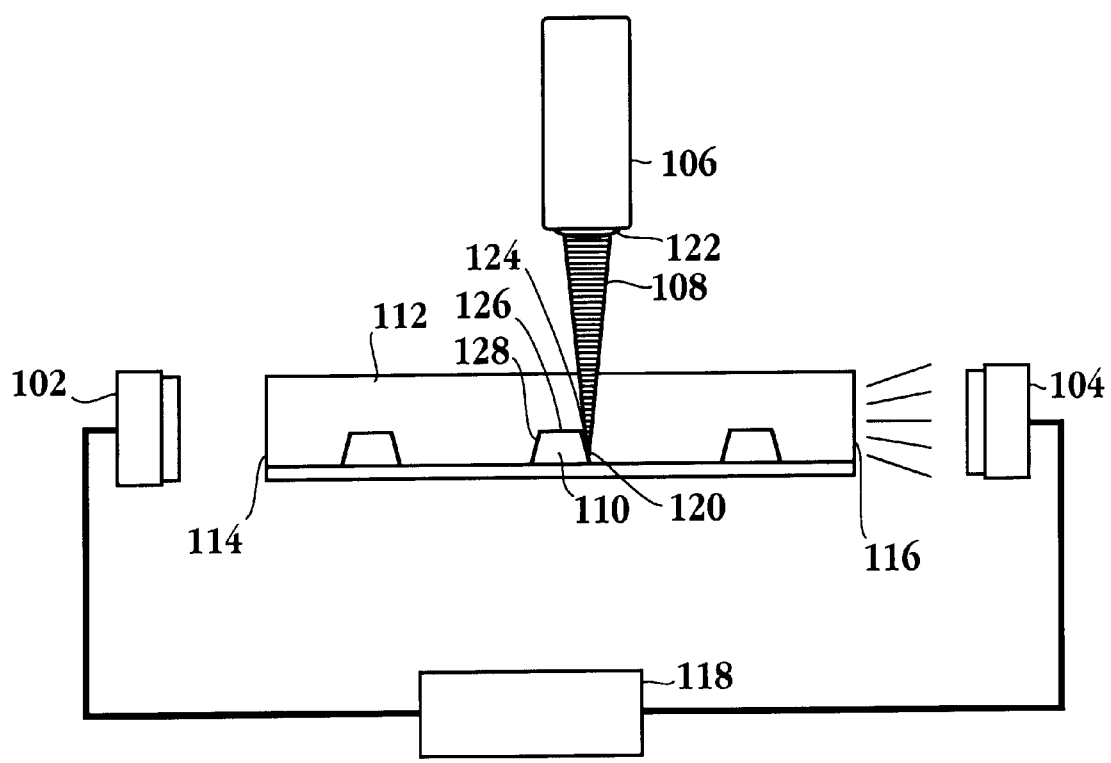

Methods and apparatus are provided for locating a sloped side wall of a channel that is disposed within a lab chip. From this point of reference, an optical detection system or an irradiation source can be aligned. The invention provides for scanning portions of a lab chip having microchannels with at least partially sloped side walls, with a light source; measuring light that exits the edges of the chip as a result of the light source interacting with any microchannels during the scan; and correlating the varying intensity of this measured light to the dimensions and characteristics of the chip's channels. A computer processor or data analyzer can also used to characterize the lab chip and align a detection system in connection with the correlation above. The functionality of this invention is due to the observation that as the light source encounters a sloped side wall of a channel during the scan step, light is directed in a manner that it emanates from an edge of the chip that is parallel to the region of the channel being scanned. The particular edge to which the light will be directed is dependent upon the delivery of the light source and the configuration and slope of the channel side walls. FIG. 1 illustrates a configuration where light emanates from the edge of the chip which is on the opposite side of the channel relative to the wall being scanned. FIG. 2 illustrates a configuration where the edge of the chip from which light emanates is on the same side of the channel as the wall that is being scanned. In any case, when evaluated in connection with the rate of the scan and the position of the light source relative to the chip, this directed light is descriptive of the location and dimensions of the side walls of the channels that are disposed within the lab chip.

The invention can be used with a lab chip having microchannels and being composed of a solid substrate or a multilayer laminate. The chip may be fabricated from fused silica, glass, acrylic, plastics, silicon or any substance that is relatively transparent to the electromagnetic radiation, e.g. silicone polymers, polyolefins, polycarbonates and the like. It may be inflexible or flexible, such as a film. If flexible, the chip is usually supported and oriented in conjunction with a rigid support. The chip's shape is preferably square or rectangular but can range to oval or circular. Depending on the purpose of the chip and the pattern of its channels, whether straight, curved or tortuous, its channel length can range from 1 to 50 cm. The width of the lab chip can vary with the number and pattern of channels, generally being at least about 1 cm, more usually at least 2 cm and may be 50 cm, frequently about 8.5 cm wide. Its thickness can vary depending on factors such as refractive indices, channel depth, and reservoirs within the lab chip which might interfere with the passage of light through the substrate.

Figure 3A:
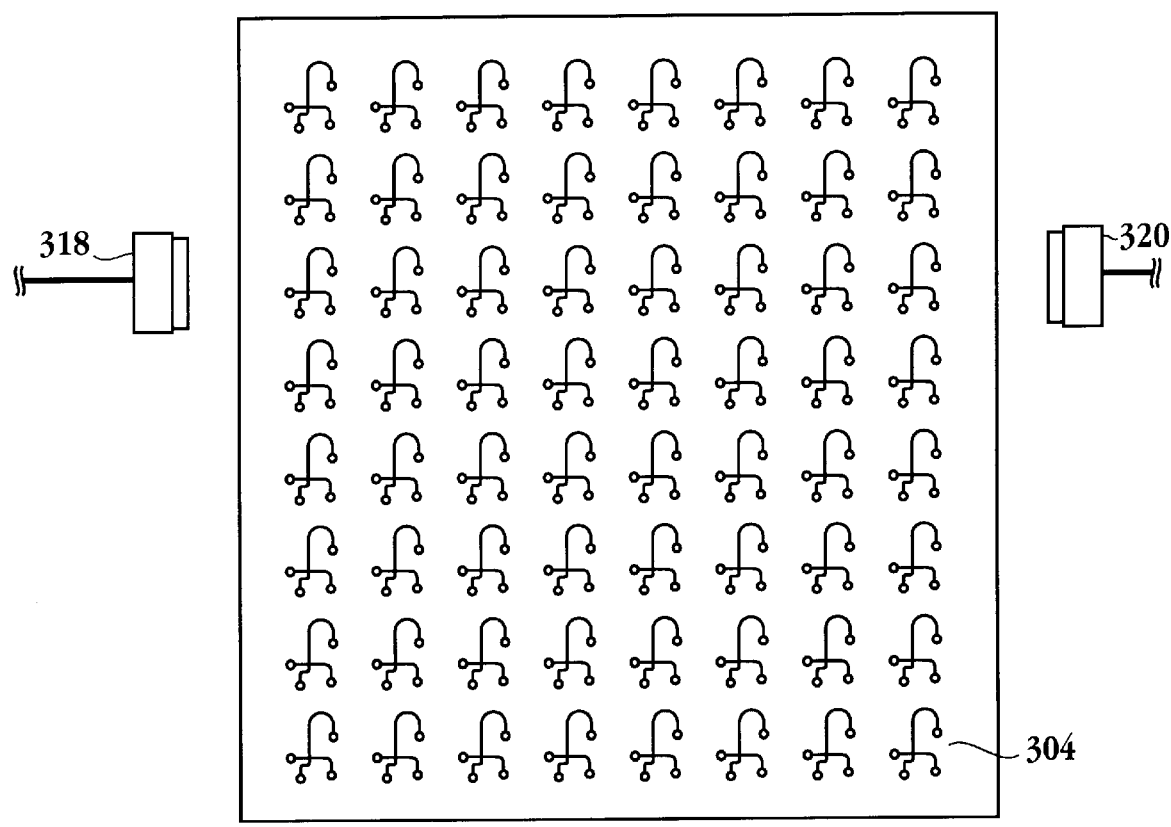
FIG. 3A is a top view of the surface of a microfluidic lab chip in which a plurality of channel networks are featured.
Figure 3B:
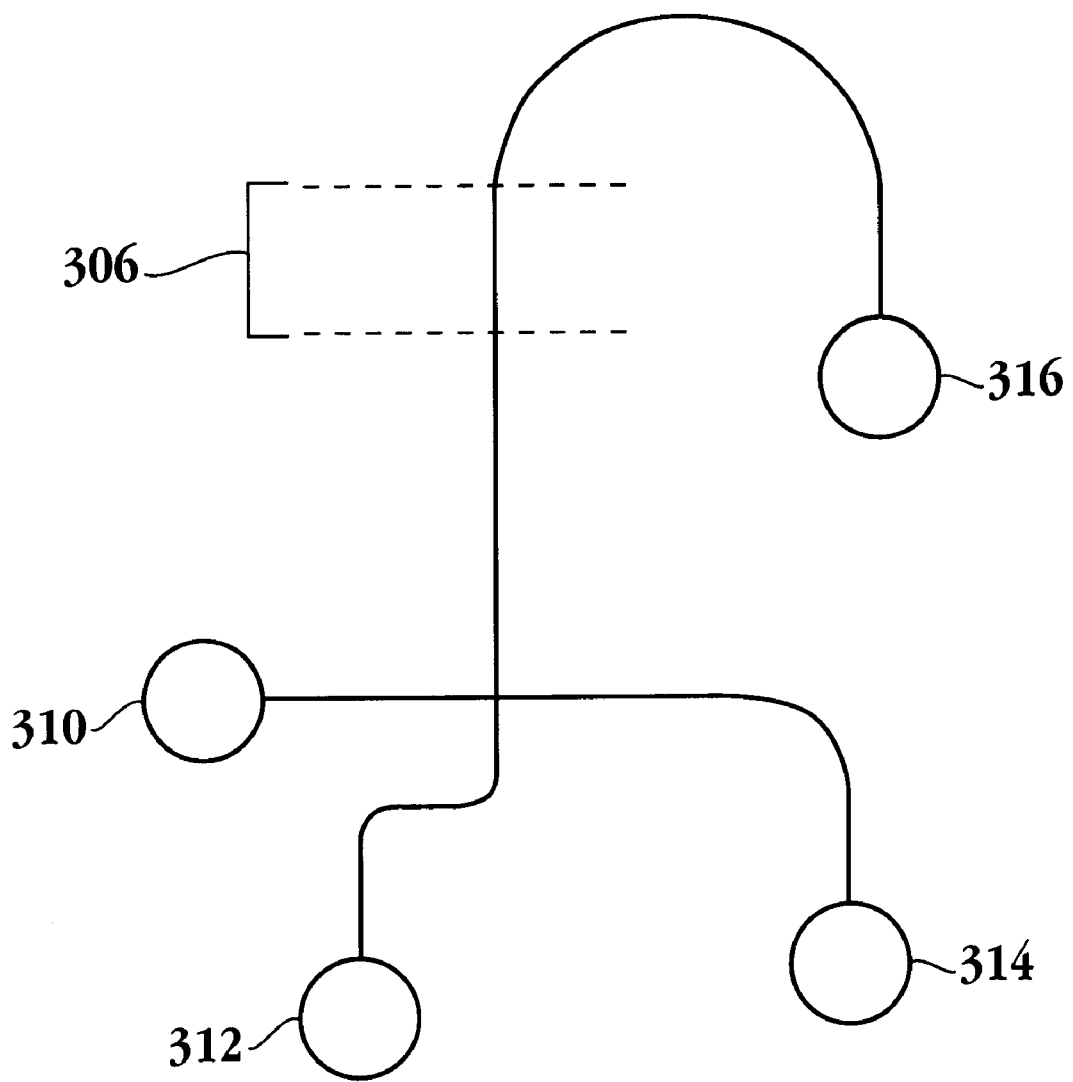
FIG. 3B is a schematic illustrating the dimensions and geometry of an exemplary channel profile.

With reference to FIGS. 3A and 3B, the microchannels in the chip can be independent or integrated into microfluidic networks 304 which are arrayed in a pattern. In the microfluidic networks, the integrated channels may be designed for specific purposes, i.e. one specific channel is dedicated to injecting a sample while another is dedicated to analysis or separation. The channels generally have a depth of about 10 to 200 $\mu$m. and a width in the range of about 1 to 500 $\mu$m, usually 10 to 200 $\mu$m. A detection zone 306 is usually incorporated into the channels which are designed for purposes of separation or other analysis. The location of this detection zone along the length of the analysis channel depends upon the application for which the lab chip is being used. For example, in DNA sequencing a long electrophoretic separation channel is required to achieve proper resolution of terminal nucleotides in long DNA fragments. In such an application, the detection zone will be at or near the end of a channel that can be up to 18 cm in length. In other types of applications such as enzyme assays, a detection zone near the end of a long analysis channel is generally not required.

Figure 5A:
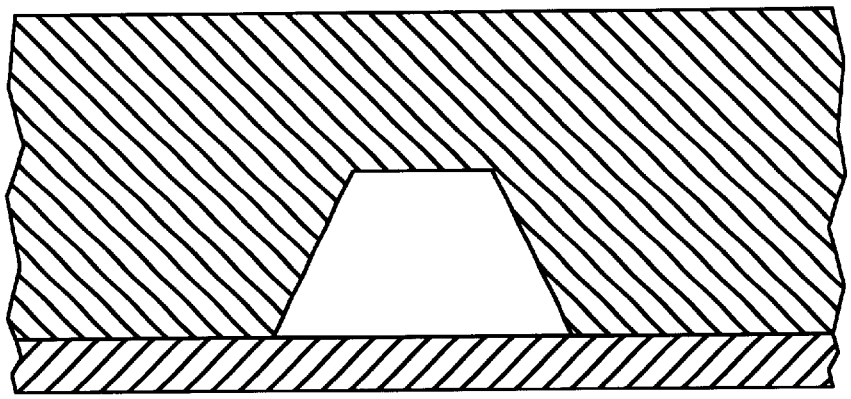
FIG. 5 is a schematic illustrating a range of profile geometries with which the invention may be used.
Figure 5B:
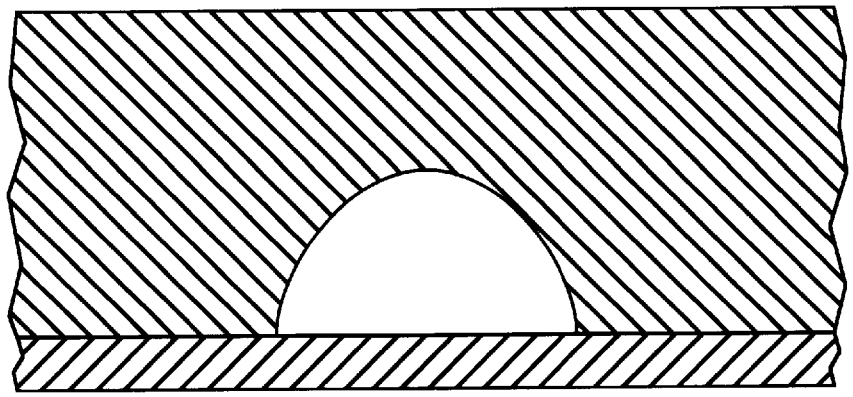
Figure 5C:
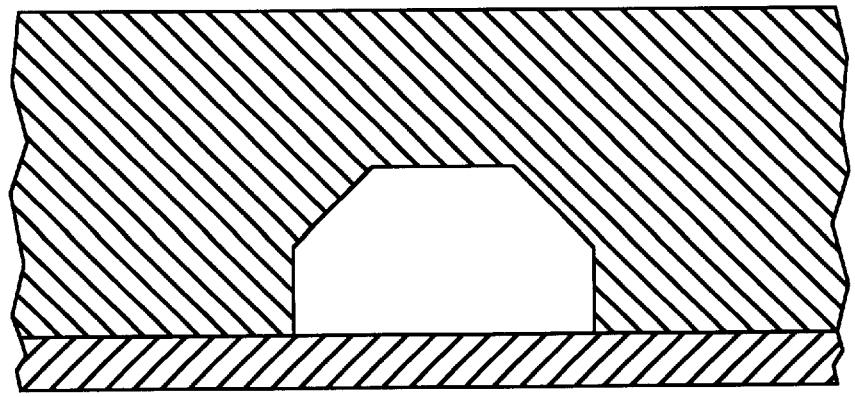

The profile of the channel cross section within the detection zones must be of a geometry such that it can direct light to the edges of the chip. As referenced in FIG. 5, this geometry can range from semi-circular to trapezoidal. Feasible variations between these geometries are dependent upon parameters involved with the relationship between the media that is held by the channel and the composition of the lab chip itself, in particular, the relative difference in refractive indices. Given an irradiation source delivered perpendicular to the lab chip surface, one such variation would include a channel having more rounded or less sloped side walls when the refractive indices of the channel contents and that of the substrate are substantially different, 0.1 or more. Under the conditions where the channel contents and the substrate have a smaller difference in refractive indices, there must be at least a portion of the side walls having a greater slope, i.e. approaching but not including an angle of 90 degrees to the chip's surface. The critical limitation is that there be a difference between the refractive indices of the channel contents and the chip in relation to the side walls of the channels having an angular slope relative to the chip's surface that ranges from greater than 0 degree to less than 90 degrees, more preferably from greater than about 22 degrees to less than about 68 degrees, most preferably around 45 degrees.

Supply and waste reservoirs 310, 312, 314, 316 are also disposed in the chip and in fluid connection with the channels. For general examples of microfluidic chips and their operation, see U.S. Pat. Nos. 5,750,015, 5,858,188, and 5,942,443 which are incorporated herein by reference.

Figure 4A:
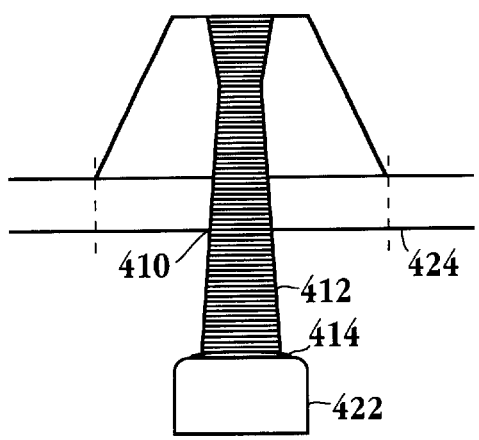
FIGS. 4A, 4B, and 4C are schematics featuring cross sectional views of different channel profiles relative to the focal length of an irradiation source.
Figure 4B:
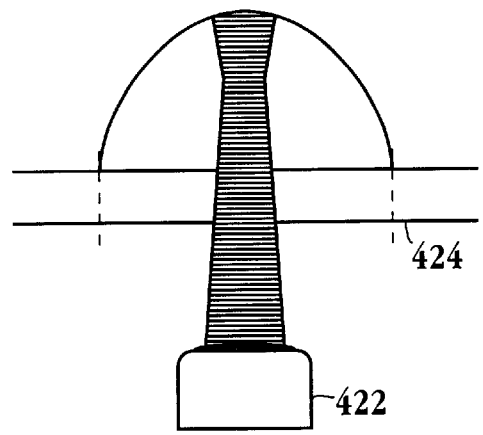

The preferable irradiation source for use in this invention is a laser, generally producing a light beam having a wavelength in the range of about 250 to 800 nm. It can however be other sources of electromagnetic radiation such as that produced by high powered lamps, LED's and the like, as long as such source can generate sufficient photons, radiation, or the like to be detected at the edge of the substrate. If a laser is used as the irradiation source, it is preferable that it be delivered directly or through a single mode fiber. If a multi mode fiber array is used, there will be apparent variations in the beam, resulting in nonuniform patterns of intensity being delivered at the beam spot. Such patterns create distortion and noise which must be addressed and normalized accordingly. With reference to FIGS. 4A, 4B. and 4C, examples of channel profiles are provided demonstrating the position of the irradiation source 422 to the lab chip 424. To allow for greater precision and accuracy, the beam 412 which is provided by irradiation source 422 is focused through a fixed lens 414 and is concentrated to beam spot 410. In some applications, this lens may be confocal and integrated into an optical detection system. The size of the beam spot can be changed by moving the irradiation source 422 either closer to or farther away from the substrate 424. The diameter of this beam spot must fall within an appropriate range relative to the channel. It must be smaller than the width of the channel yet large enough to produce adequate detection limits at the edges of the chip. In general, a beam spot having a smaller diameter will result in better resolution and sensitivity. For purposes of convenience and standardization, the beam spot is preferably within the same parameters required by the excitation beam of the optical detection system during actual sample analysis using the microfluidic device.

Figure 6:
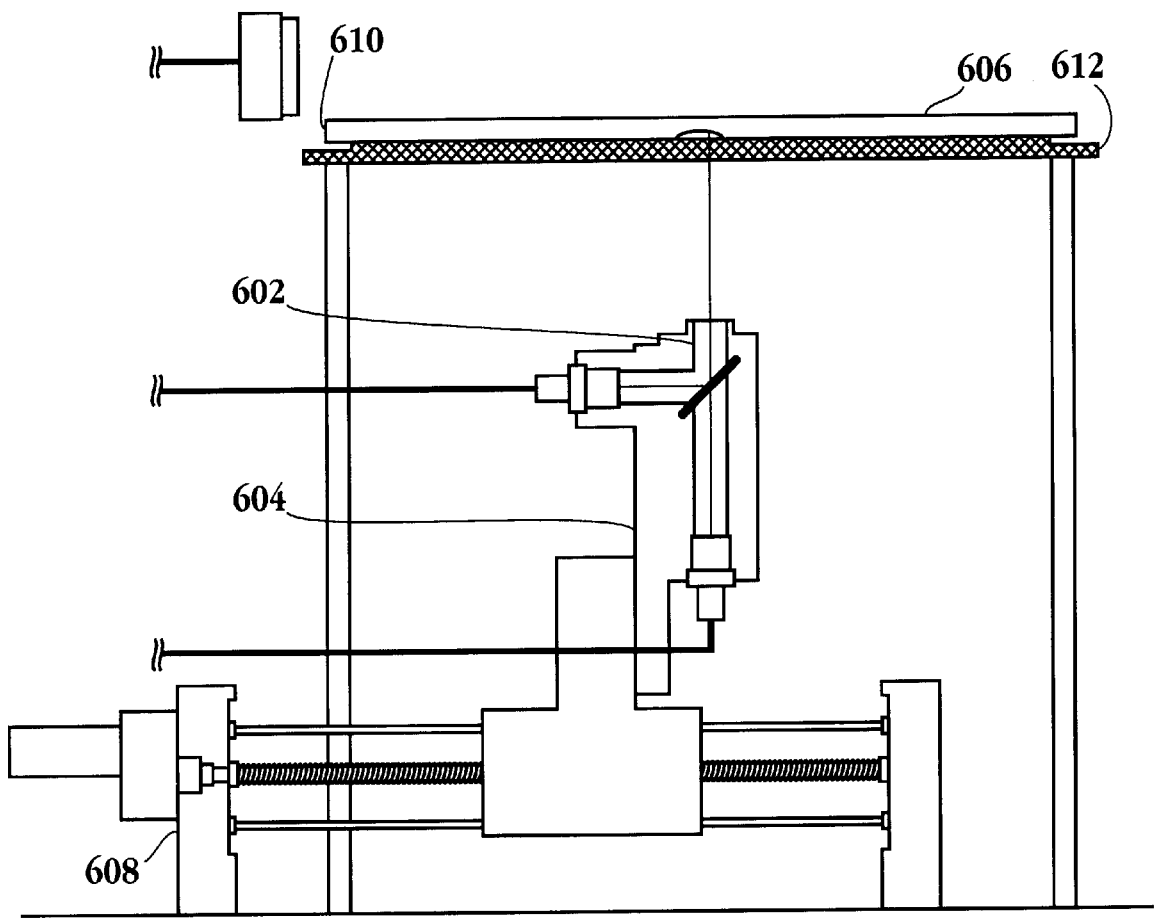
FIG. 6 is an elevational side view of a carriage system featuring a lab chip, an optical detection system, a scatter detector, and the relative orientation of these elements.

With reference to FIG. 6, the irradiation source can be incorporated into an optical fluorescent detection system 604 which comprises in addition to the irradiation source a means for interrogating a capillary channel for the presence of fluorescence. These detection systems are described in a number of patents for interrogating capillaries, e.g. U.S. Pat. Nos. 5,296,703, and 5,730,850 which are incorporated herein by reference.

The lab chip 606 is removably mounted to a carriage system 612 comprised of a micropositioner stage 608 allowing for translational movement within the carriage system. Such movement can be in multiple axes and controlled manually or through a computer by various means including mechanical, electromechanical, electromagnetic, and the like. Preferably, the stage incorporates a servo or stepper motor with a position encoder and home switch enabling position registry and immediate monitoring and feedback control of movement within the system through the use of a computer or data processor. Such stages are well known to those skilled in the art and are commercially available through vendors such as Edmund Industrial Optics, Northern Magnetics, Inc., NUTEC, and others.

The carriage system also incorporates the irradiation source. Depending upon the desired configuration, the micropositioner stage 608 preferably allows one or both of the lab chip 606 and the irradiation source 604 to move in relation to each other. In an alternative, the carriage system can allow only the irradiation source 604 to move in relation to the chip 606. In yet another alternative, the irradiation source can be fixed to the carriage system where it is pivotally mounted to facilitate the scanning of the chip. Due to the miniature specifications of the lab chip and its incorporated microchannels, the relative range of motion required by the pivotal mount is insignificant so that the scanning is still accomplished in substantially parallel plane.

For purposes of measuring light emanating from the edge of the lab chip, various detectors with appropriate sensitivity can be used. Examples of such detectors include photomultiplier tubes (PMT's), charged coupled detectors (CCD'S) avalanche photodiodes, pin diodes and the like. These scatter detectors must be properly positioned so as to ensure proper detection. As illustrated in FIGS. 3A and 3B, scatter detectors 318 and 320 are preferably aligned at a location which is orthogonal to the relevant detection zone 306 within the channel being scanned. It is also preferably at a position where reservoirs disposed in the chip will not interfere with relevant scattered light. The detectors should also be at a distance from the edge of the lab chip which will allow the detectors to measure photons exiting the chip's edges. The range of this distance is dependent upon the type and strength of the irradiation source used as well as environmental factors such as ambient or artificial light present in the immediate surroundings. It may be necessary to adjust the positioning of these detectors relative to the edge of the lab chip to achieve an optimal signal. By employing light filters that discriminate against unwanted wavelengths, the detectors can be configured to exclude ambient light thereby increasing specific sensitivity and simplifying the process of alignment.

With reference to FIG. 1, the general embodiment of the invention is presented where two scatter detectors 102 and 104 are utilized. Irradiation source 106 provides beam 108 which is focused to a beam spot 120 and used to scan the cross sections of detection zones relative to specific channels 110 in substrate 112. Scatter detectors 102 and 104 are oriented so as to detect any light transmission emanating from substrate edges 114 and 116. A data processor or analyzer 118 is configured to receive any signals from scatter detectors 102 and 104. The movement of the irradiation source relative to the microchannels throughout the scanning process is also monitored by data processor in order to correlate the scatter data points to corresponding locations in the channel's profile.

Figure 9:
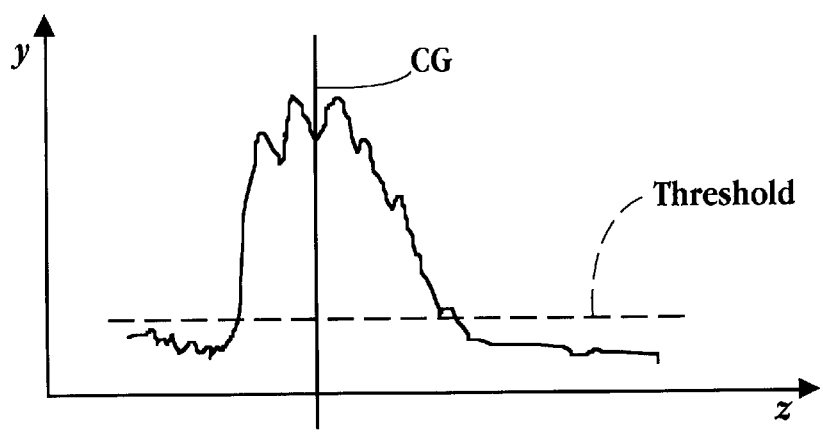
FIG. 9 shows a typical light-scatter signal, illustrating an algorithm determining the center of gravity of the signal.

FIG. 9 shows a typical scatter signal recorded from the side of a chip. As seen, the signal is relatively noisy, particularly in the peak region. In order to find the "center" of the peak, a algorithm that calculates the center of gravity of the signal between two threshold points is carried out. The threshold points determine the beginning and the end of the calculation. They are usually identical and are set such that the calculation region is clearly above the noise in the detector (as shown dashed in the drawing). Care must be taken to avoid noise at the endpoints terminating the calculation too soon. This can be easily accomplished by allowing a certain minimum number of counts to be done before checking to see if the endpoint is reached. The calculation is:

$$CG = \frac{\sum_{i=0}^{n} x_i y_i}{\sum_{i=0}^{n} y_i}$$

where n is the number of points between the start and endpoints, and x and y are the w and y coordinates of curve, respectively.

This is the CG for the scatter signal, and is set as the peak of the scatter signal, representing the position of the channel side wall. This peak must be calibrated for each channel geometry. In one method, described with respect to FIG. 8, the channel is filled with a high concentration of fluorescein (>1 uM), and the channel is scanned to record both scatter and fluorescence signals simultaneously. From this, the program determines the offset between the determined sidewall position and optimal signal position in the channel. This offset is then applied to other channels, for example, in a multi-channel card, to determine the optimal signal-sensing position within the channel, based on (i) the measured position of the channel sidewall (sidewall CG), and the predetermined optimal offset from the sidewall to the signal-sensing position.

With reference to FIG. 6, the process according the general embodiment of the invention comprises the steps of registering and monitoring the position of the carriage system with regards to the irradiation source 604 and the lab chip 606, scanning the lab chip across the profiles of the detection zone cross sections with the irradiation source, measuring scattered light at the edges of the lab chip 610 with scatter detectors, and correlating the data points from the scatter signals to the specific locations of the channel side walls within the lab chip.

Registering and monitoring the position of the carriage system with regards to the irradiation source 602 and the lab chip 606 is preferably accomplished through the use of the home switch and position encoder that is integrated into the micropositioner stage 608. In the alternative, a manual approach can be used where the lab chip itself incorporates a calibration line or other feature with which the irradiation source can be initially aligned and registered. In any case, the subsequent movement within the carriage system is monitored relative to the point of registry to generate data points used in subsequent analysis.

A scan is then conducted where the beam spot can be delivered from either the bottom, as in FIG. 1, or the top side, as in FIG. 2, of the chip. In an automated system, the computer processor will likely require the general specifications of the lab chip for purposes of generally aligning one or more optical detection systems so that the scan will intersect the appropriate detection zones. This is particularly true where the chip encompasses an array of microfluidic patterns having multiple detection zones in various locations. In a manual system however, the beam is visually aligned by the operator prior to scanning. With reference to FIG. 1, the scan is conducted in a plane that is normal to relevant channels within the chip. It is initiated near one edge of the chip 124, proceeds across the detection zones 126, and terminates towards the opposite edge of the chip 128. The scan is preferably conducted at a fixed rate and beam intensity as the irradiation source travels over the channel due to the fact that the scatter detectors need to be configured for a specific resolution and sensitivity. If the scan rate is not constant, then this configuration becomes much more complicated and expensive. A lens element 122 is further defined in FIGS. 4A–C.

Simultaneous to the scanning, scattered light is measured at the chip's edges. The scatter signals are then delivered to a data processor or analyzer where they are correlated to the movement of the carriage system during the scan and used to determine the specific locations of the channel side walls within the lab chip. These locations can then be used as points of reference from which optical detection systems can be aligned. The light pattern correlated to the channels can also be used to analyze the general profiles of the channels and their associated side walls. For instance, in the case of symmetrical channels, this light can be used to determine the location of the geometric centers.

In an automated and high throughput configuration, many variations of this invention are possible. For example, a system can be provided where the channels of a lab chip are arrayed in a pattern similar to that illustrated in FIG. 3A, having networks patterned in a column and row configuration. A battery of optical detection systems may be employed where there is one detection system designated to each row of networks acting generally in unison with yet independent to the entire battery. For the purposes of the scanning step, the entire battery initiates its row scans at one edge of the chip, intersects each detection zone in the row, and finishes the scan at the other edge of the chip. Scatter detectors directed at the ends of each row provide the necessary feedback to the computer processor whereby the data is recorded and used to characterize entire rows of microfluidic patterns.

In a preferred embodiment of the invention, a standard location for reproducible irradiation is determined for analogous microchannels. It is readily defined as being at a set distance from the side walls of each channel. This is accomplished by first conducting a survey of a model channel that is loaded with an optically detectable standard such as fluoroscein, rhodamine and the like. The lab chip containing the model channel is then removably mounted to a carriage system and apparatus similar to that illustrated in FIG. 6. In this embodiment, the irradiation source is preferably incorporated into an optical detection system which also includes a light detector that directly measures fluorescence from the irradiated channel (channel signal). Initially, the optical detection system is manually aligned so that its beam spot is at a point immediately adjacent to the channel.

Figure 4C:
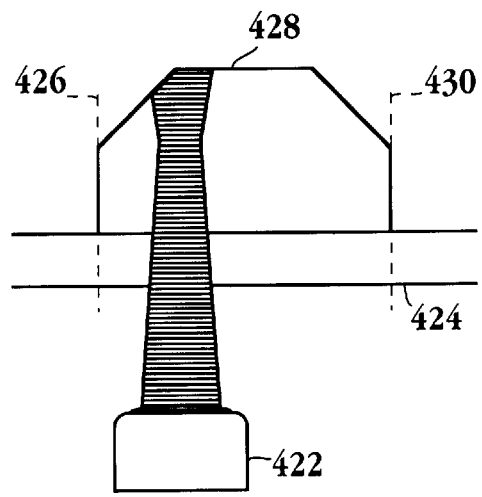

The location of the laser relative to the lab chip is then registered and automatically recorded by the data processor. A scan is then conducted where the beam spot is moved in a plane that is orthogonal to the channel. With reference to FIG. 4C, this scan is initiated at a point just prior to one channel side wall 426, continues across the floor 428, and is completed just after the opposite side wall 430. Simultaneous to this scan, light is detected by the scatter detector at the edge of the chip while fluorescence is measured within the channel by the light detector in the optical detection system. Both the fluorescence from the channel (channel signal) and the light detected at the edge of the substrate (scatter signal) are provided to the data processor for analysis.

Figure 8:
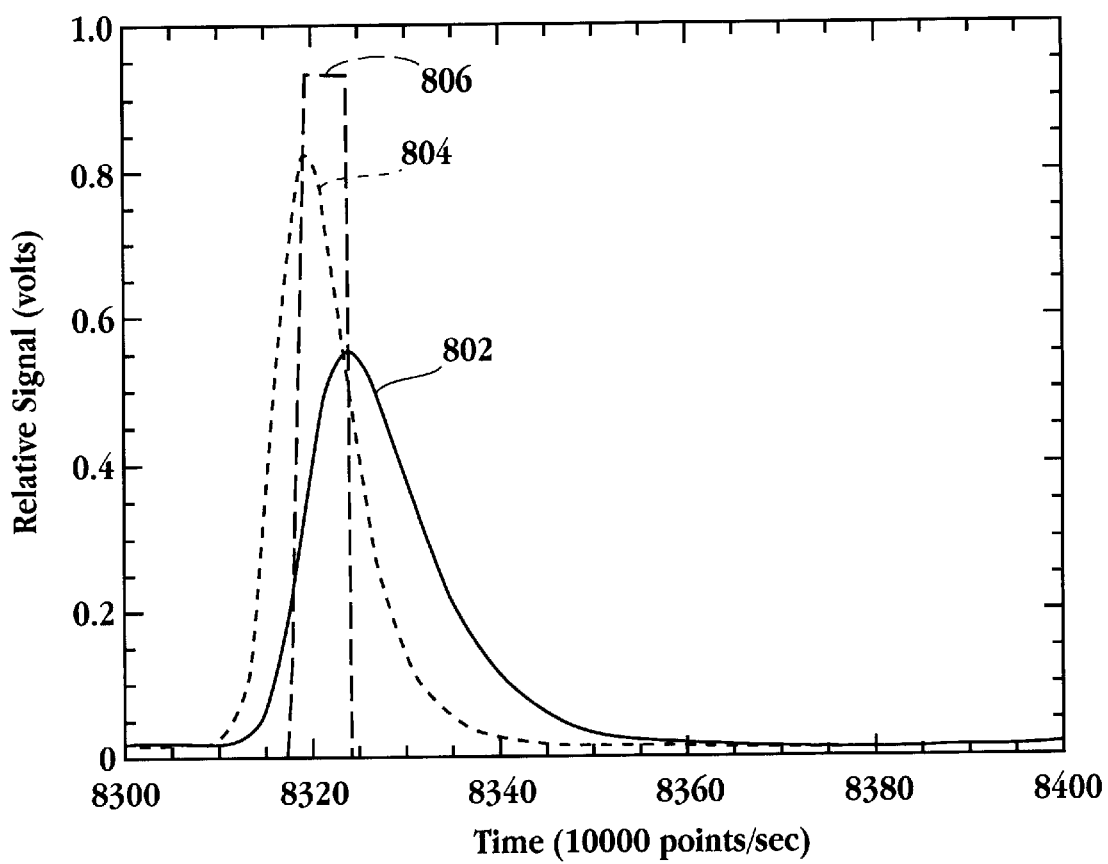
FIG. 8 is a graph of the observed signals from an optical detection system and a scatter detector generated from a lab chip having a microchannel loaded with fluoroscein dye.

For purposes of illustration, exemplary data is presented in FIG. 8. An effective location for optical interrogation within the channel profile is initially determined by referring exclusively to the data curve for the channel signal 802. This requires a correlation between the channel signal data points and the relative locations within the channel profile from which these data points are generated. The relative locations within the channel profile that generate the highest fluorescence define effective areas within the channel for purposes of interrogation. Subsequent to this initial determination, the scatter signal 804 can be calibrated according to the channel signal 802.

Calibration is possible because the scatter signal 804 is sampled at the same rate and with the same laser source as the channel signal 802. An expected spatial offset 806 between the relative data curves for channel signal and scatter signal is generated. This offset is due to the fact that the maximum scatter signal 804 is caused by the laser interaction with a particular side wall of the channel while the maximum channel signal 802 is caused by laser irradiation of the largest volume of the fluoroscein standard, usually located in the optical center area of the channel. In any case, the offset between the scatter and channel signals correlates to the positional relationship between the side wall and the channel center. This positional relationship will generally be the same in all analogous channels. As a result, it can be used as a separation standard for all analogous channels once the relative point of reference (a specific data point related scatter signal generated from the side wall) is established. Within each microchannel, establishing the relative point of reference is accomplished by utilizing the general embodiment of the invention that is first mentioned above. This approach facilitates the alignment of optical detection systems relative to microfluidic channels.

A variation of this embodiment is possible where the channel signal 802 is generated and monitored independent to the scatter signal 804. This however requires precise and independent standardization of the data from these signals for necessary comparative and qualitative purposes.

EXAMPLE 1

The following method demonstrates a preferred embodiment of the present invention where light intensity from a fluorescent medium within a channel was used to calibrate scatter signal so that it could be subsequently used as a means to align the optical detection system relative to the detection zones of analogous channels disposed in different lab chips.

Figure 3C:
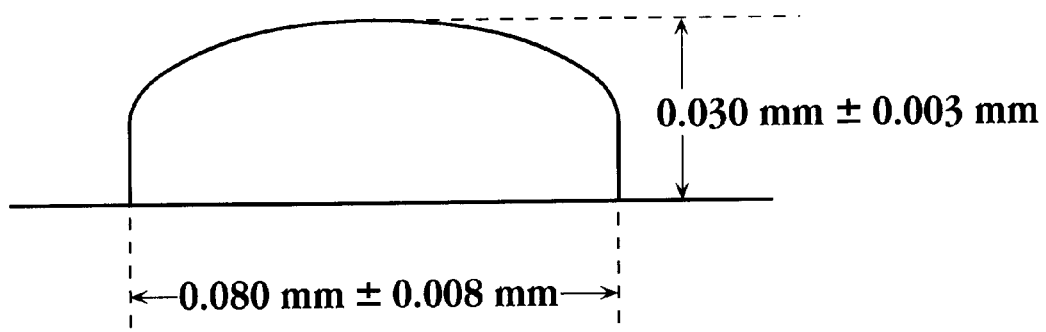
FIG. 3C is a schematic illustrating the dimensions of an exemplary cross section of a microfluidic channel.

With reference to FIG. 6, a model lab chip was placed upon a carriage platform 612 that was 1 mm thick and made of quartz. The chip 606 was 8.5 mm wide and 8.5 mm long. It was composed of an acrylic substrate that was laminated on its lower surface with an acrylic film, both layers having a refractive index of 1.49. The substrate was 1.5 mm thick and made of PMMA. The film was 40 $\mu$m thick and made of PMMA, Shrinkolite 40. The chip was comprised of 64 microfluidic patterns that were essentially identical. These patterns were uniformly arrayed in a layout having 8 rows by 8 columns. The channels of these patterns were approximately 25 $\mu$m deep, 80 $\mu$m wide at the lower surface of the substrate, 50 $\mu$m wide at the top of the channel and essentially symmetrical in shape. The dimensions and geometry of the channel profiles are shown in FIG. 3C. Each pattern was comprised of a channel network having an analysis channel with a specific detection zone. The channels to be profiled were preloaded with a dilute aqueous solution of fluoroscein dye having a refractive index of around 1.33–1.35.

A light source, mounted to the carriage system, was directed in a plane essentially perpendicular to and towards the lower surface of the substrate. The carriage system allowed the light source to be moved in relation to the chip. The location of the light source was 2.24 mm from the chip to allow proper focus of a beam spot that had a diameter of 8 $\mu$m at its interface with the lab chip's surface. The light source used was an air cooled, single mode argon-ion laser having a wavelength of 488 nm and powered at 4 milliwatts. It was manufactured by OMNICHROME (model no. 543-BS-A$\phi$3). This laser was also incorporated into an optical detection system similar to that in FIG. 6 which allowed for the excitation of the fluoroscein dye at the detection zones within the analysis channels. Integrated into this optical detection system was a light detector that transmitted a channel signal to a data processor in response to the fluorescence that emanated from the detection zone. In this case, the detection zone was located approximately 6 mm from the point where a sample could be injected into the analysis channel.

One scatter detector, manufactured by BURR-BROWN (model no. OPT101), was placed 20 mm from the edge of the card in a similar configuration to that illustrated in FIG. 3A. This detector was comprised of a silicon pin photodiode connected to a transimpedence amplifier making up a unit. This unit was then connected to a low pass filter which in turn was connected to a data processor. In this configuration, its electrical bandwidth was limited to 3000 Hz.

The laser was then manually aligned so that its beam spot was in the detection zone at a point adjacent to the analysis channel. The location of the laser relative to the lab chip was then registered and automatically recorded by the data processor after which a scan was conducted where the beam spot was moved in a plane that intersected the channel. This scan was initiated at a point just prior to one channel side wall and completed just after passing the opposite side wall. It was done at a constant rate of 20 mm/sec. Simultaneous to this scan, light was detected by the scatter detector at the edge of the chip while fluorescence was observed within the channel by the light detector in the optical detection system. Both the fluorescence from the channel (channel signal) and the light detected at the edge of the substrate (scatter signal) were sampled at a rate of 10000 samples/sec and provided to the data processor for analysis.

The data obtained as described above is presented in FIG. 8. An effective site for optical interrogation within the channel was initially determined by referring exclusively to the data curve for the channel signal 802. This required a correlation between the channel signal data points and the relative locations within the channel profile from which these data points were generated. The relative locations within the channel profile that generated stronger channel signals defined effective areas within the channel for purposes of interrogation. Subsequent to this initial determination, the scatter signal 804 was calibrated according to the channel signal 802. This calibration in essence allowed for the determination of the effective site for irradiation once the location of the channel side wall within the lab chip was established.

Following this calibration and the characterization of the model chip, the lab chip was removed and a second similar lab chip was removably mounted to the carriage system. As above, the position of the lab chip within the carriage system was registered and the laser source was aligned at an analogous detection zone within second the arrayed lab chip. A laser scan was then completed whereby a scatter signal for a side wall analogous to the one generated with exemplar chip was obtained. In a continuous feedback mode and through the use of the calibration factor, this second scatter signal was correlated by the data processor to the relative center of the newly scanned microchannel. Through this correlation, the optical detection system was aligned at an optimal position within the channel profile where it could detect fluorescent analytes, minimizing background noise and optimizing channel signal in an inexpensive manner that was reproducible in analogous channels on the same or different lab chips.

EXAMPLE 2

In the following example, the same equipment as above is used where two scatter detectors located on opposite sides of the lab chip are used to characterize a symmetrical channel profile and align the optical detection system relative to the channel's geometric center. Unlike the example above, a fluorescent standard loaded into the channel is not required.

Figure 7:
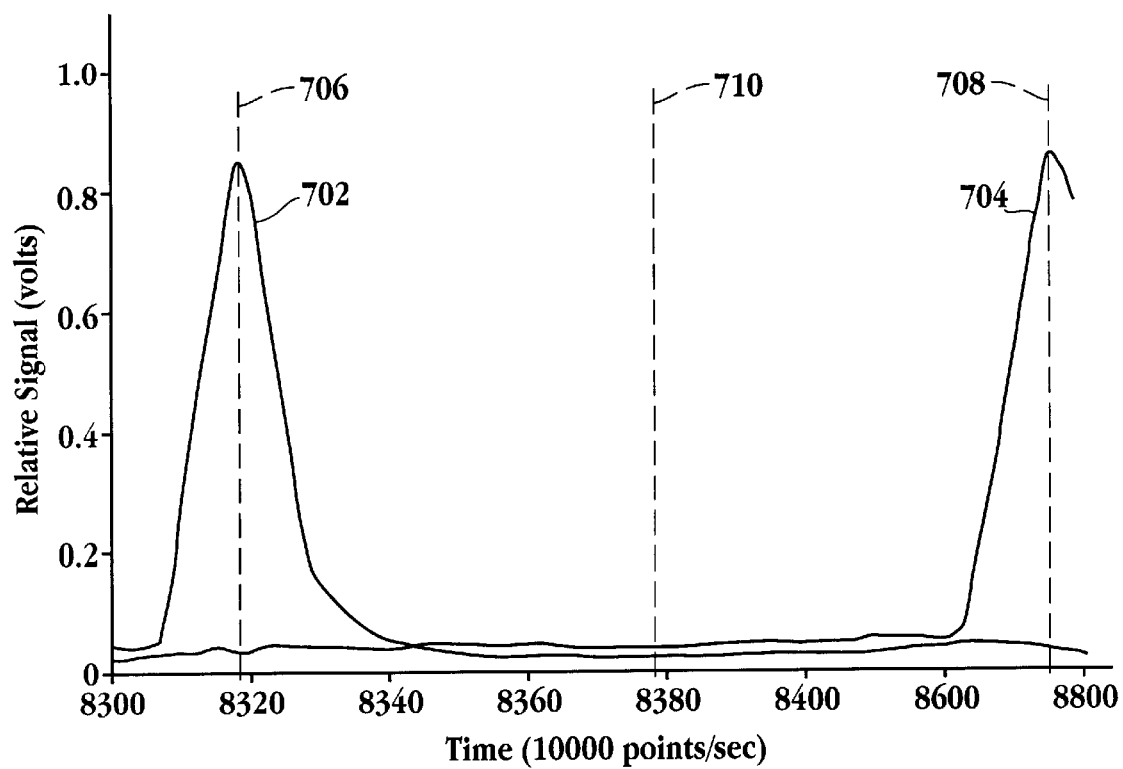
FIG. 7 is a graph demonstrating scatter data points that might be generated through the application of the invention using two scatter detectors positioned at opposite sides of the lab chip.

A model lab chip is removably mounted to the carriage system after which its position relative to the laser source is placed in registry. The laser is then aligned at a detection zone adjacent to one of the microfluidic analysis channels. With reference to FIG. 7, samples of probable data are presented. As above, a laser scan of the channel profile is conducted provided however that scatter signals are generated at opposite edges of the lab chip presenting two Gaussian shaped peaks 702 and 704, one corresponding to each side wall of the channel. Due to the symmetry of the channel cross section, the center of the channel for purposes of optical interrogation is determined by locating the midpoint 710 between the centroids 706, 708 generated by the two scatter signals. Through a method similar to that in Example 1, the channel center is then established with regards to the point of reference (channel side wall). The spatial offset is then established between this midpoint and one or both of the side walls. This separation standard is subsequently used to align optical detection systems relative to analogous channels as described above.

In a qualitative respect the present invention provides for increasing sensitivity in the optical detection systems whereby a low strength signal can be distinguished from background noise. An example of such an application is with DNA sequencing. Statistically the chemistry used in sequencing produces a significantly greater number of short fragments as opposed to longer ones. As a result, during separation the lower concentrations of the longer fragments generate weaker signals. By using this invention to properly align the optical detection system, there is an increased sensitivity of the optical detection systems for detecting the longer fragments.

For purposes of quantifying results, the invention provides a means for generating comparable results where more than one microfluidic channel is being analyzed. It can be used when chemical operations are run in different and independent microfluidic channels but require quantitative analysis. One example of this is where a number of microfluidic channels or networks have been configured with a specific biochemical model to screen for an effect of a test compound on an interaction between two components of a biochemical system, e.g., receptor-ligand binding or substrate turnover. The assayed function is then compared to a control, e.g., the same reaction in the absence of the test compound or in the presence of a known effector. Compounds which show promising activity in the screening assay can then be subjected to further testing to identify effective pharmacological agents for the treatment of disease or symptoms of a disease. In these assays, the effect of one compound upon another is generally indicated by the production or inhibition of a particular event or signal. Proper alignment of the detection systems relative to the detection zones in the lab chip is required for the purposes of generating signals and data that can be compared from channel to channel. Such alignment can be accomplished through the use of the present invention.

Another relevant application is in the field of genetic analysis and SNP detection where assays are utilized to determine genetic makeup. Many of the genetic assays utilized today are based upon chemistries which use colorimetric or fluorescent labels. The intensity of the signals generated from these labels can be directly correlated to the presence or absence of specific nucleic acids. Parallel analyses is required to verify certain results as well as test many different sites within the same sample, also known as multiplexing. Such analyses requires comparable results that are possible through the application of the provided methods and apparatus.

In general, this invention can be used to standardize detection in assays and other chemical operations being run in different channels within the same lab chip as well as those within different lab chips. As described above, the use of scatter detectors to align optical detection systems is an inexpensive and effective approach in microfluidic applications where optical detection is required. The invention as presented is also highly suitable for purposes of automation where speed and efficiency are essential. For qualitative purposes, it allows determination of a location within a microfluidic channel where an effective signal can be obtained for purposes of optical detection. For quantitative purposes, the invention can be used to determine analogous locations in different microfluidic channels where substantially similar volumes can be irradiated in a reproducible manner.

All publications and patents mentioned in this application are herein incorporated by reference to the same extent as if each individual publication or patent was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the location of a sloped side wall of a microchannel disposed in a light transmitting substrate, said method comprising:

scanning a portion of said substrate with a light source in a direction that is angled with respect to the direction of channel flow, said portion including said side wall of said microchannel;

monitoring the relative movement between said substrate and said light source during said scanning while measuring light emanating from at least one edge of said substrate;

correlating said emanating light to the relative positions between said light source and said substrate during said scanning, and determining the location of said side wall within said substrate from said correlating.

2. The method of claim 1, wherein the substrate is comprised of a laminate having at least two layers.

3. The method of claim 2, wherein where said layers have the same refraction indices.

4. The method of claim 2, wherein said layers have different refraction indices.

5. The method of claim 1, for use in detecting fluorescent sample components moving within said channel, by irradiating a region of the channel with a focused laser beam and detecting light emitted from the channel, wherein said beam is placed a selected lateral distance from the determined location of said side wall.

6. The method of claim 5, wherein said selected lateral distance is determined from the lateral distance in the microchannel between the determined location of a microchannel side wall and the lateral position of said beam within the channel that gives a maximum fluorescence signal.

7. The method of claim 5, wherein said selected lateral distance is determined as the midpoint in the channel between the determined location of the microchannel side wall and the determined location of the opposite channel side wall.

8. The method of claim 5, wherein said substrate has a plurality of microchannel units, the selected lateral distance is determined for one of the units, and applied to the other units when detecting fluorescent sample components moving within channels of such other units.

* * * * *